United States Patent [19]

Kiely et al.

[11] Patent Number: 4,617,405
[45] Date of Patent: Oct. 14, 1986

[54] PREPARATION OF ALPHA, BETA-UNSATURATED CARBONYL COMPOUNDS

[75] Inventors: Donald E. Kiely, Birmingham, Ala.; Martin Seidman, Decatur, Ill.

[73] Assignee: A. E. Staley Manufacturing Company, Decatur, Ill.

[21] Appl. No.: 654,811

[22] Filed: Sep. 25, 1984

[51] Int. Cl.$^4$ .................. C07D 307/60; C07C 35/06
[52] U.S. Cl. ........................... 549/262; 549/231; 558/315; 560/211; 562/599; 568/315; 568/433; 568/460
[58] Field of Search ............... 549/262, 231; 260/465.9; 560/211; 562/599, 595; 568/315, 433, 460; 558/315

[56] References Cited

U.S. PATENT DOCUMENTS 2,452,672 11/1948 Miller et al. ............... 260/465.9
2,858,330 10/1958 Fischer ..................... 560/211
3,487,101 12/1969 Volker et al. ............... 560/211
3,954,854 5/1976 Gehrmann et al. ........... 562/599

OTHER PUBLICATIONS

Linstead et al., J. Chem. Soc., pp. 1211–1218 (1953).
Fieser et al., Advanced Org. Chemistry, Reinhold, p. 289 (1961).
Anschutz et al., Ann., vol. 254, pp. 155–168.
Morrison et al., Org. Chem., pp. 865–874 (3rd Ed., Allyn and Bacon, Inc.) (1973).

*Primary Examiner*—Henry R. Jiles
*Assistant Examiner*—Bernard I. Dentz
*Attorney, Agent, or Firm*—Philip L. Bateman; James B. Guffey; Michael F. Campbell

[57] ABSTRACT

Alpha, beta carbonyl compounds are prepared from an acid anhydride selected from the group consisting of glutaric anhydride and 3-alkyl glutaric anhydride, and a beta-hydroxy carbonyl compound having the following chemical formula:

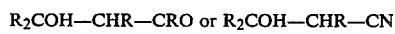

$R_2COH-CHR-CRO$ or $R_2COH-CHR-CN$ where each R is any substitutent group.

The process comprises: (a) reacting the acid anhydride and the beta-hydroxy carbonyl compound in the presence of a catalytically effective amount of an acid catalyst to form an ester; (b) reacting the ester in the presence of a catalytically effective amount of a base catalyst to form a alpha, beta-unsaturated carbonyl compound and a carboxylic acid; and (c) separating the alpha, beta-unsaturated carbonyl compound and the carboxylic acid.

8 Claims, No Drawings

PREPARATION OF ALPHA, BETA-UNSATURATED CARBONYL COMPOUNDS

FIELD OF THE INVENTION

This invention relates to alpha, beta-unsaturated carbonyl compounds. More particularly, this invention relates to a process for preparing alpha, beta-unsaturated carbonyl compounds from an acid anhydride selected from the group consisting of glutaric anhydride and 3-alkylglutaric anhydride, and a beta-hydroxyl carbonyl compound.

BACKGROUND OF THE INVENTION

A. Alpha, Beta-Unsaturated Carbonyl Compounds

An alpha, beta-unsaturated carbonyl compound is a compound having the following chemical formula:

$R_2C=CR-CRO$ or $R_2C=CR-CN$ where each R is any substituent group.

Alpha, beta-unsaturated carbonyl compounds are described generally in Morrison, R. T. and Boyd, R. N. *Organic Chemistry*, pp. 865 et seq. (3d Ed. Allyn and Bacon, Inc. 1973). Typical substituent groups include hydrogen and alkyl, aryl, and aralkyl groups. An alpha, beta-unsaturated carbonyl compound is distinguished by the fact that the carbon-carbon double bond is conjugated with the carbon-oxygen double bond or the carbon-nitrogen triple bond. Because of this conjugation, alpha, beta-unsaturated carbonyl compounds possess special chemical properties in addition to the properties of their individual functional groups.

Some of the more commercially important alpha, beta-unsaturated carbonyl compounds are set forth below:

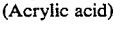

| $H_2C=C(CH_3)COOCH_3$ Methyl 2-methyl-propenoate (Methyl methacrylate) | $H_2C=CHCOOCH_2CH_3$ Ethyl propenoate (Ethyl acrylate) |
| --- | --- |
| $H_2C=CHCN$ Propenenitrile (Acrylonitrile) | $C_6H_5CH=CHC(O)CH_3$ 4-Phenyl-3-buten-2-one (Benzalacetone) |
| $H_2C=CHCHO$ Propenal (Acrolein) | $H_2C=CHCOOH$ Propenoic acid (Acrylic acid) |
| $CH_3CH=CHCHO$ 2-Butenal (Crotonaldehyde) | HC=CHC(O)OC(O) cis-Butenedioic anhydride (Maleic anhydride) |
| $C_6H_5CH=CHCHO$ 3-Phenylpropenal (Cinnamaldehyde) | HOOCCH=CHCOOH Butenedioic acid (Maleic or Fumaric acid) |

B. Preparation of Alpha, Beta-Unsaturated Carbonyl Compounds

Although there is no single method for preparing all types of alpha, beta-unsaturated carbonyl compounds, there are methods available for producing certain classes of these compounds. See generally Morrison, R. T. and Boyd, R. N. *Organic Chemistry*, pp. 865 et seq. (3d Ed. Allyn and Bacon, Inc. 1973). For example, alpha, beta-unsaturated aldehydes and ketones can prepared by dehydrating aldol condensation products; alpha, beta-unsaturated carboxylic acids and esters are prepared by the dehydrohalogenation of alpha-halo acids or esters; and aromatic alpha, beta-unsaturated carboxylic acids are prepared by the Perkin condensation reaction. An example of each of these reactions is shown below.

Reaction 1—Preparation of Crotonaldehyde

Acid catalyzed dehydration of 3-hydroxybutanal, an aldol condensation product from acetaldehyde.

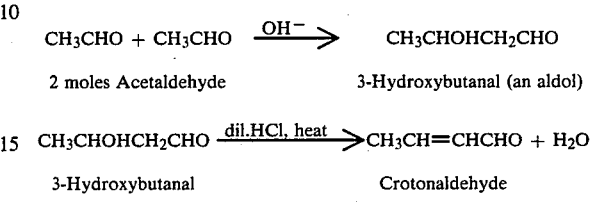

$CH_3CHO + CH_3CHO \xrightarrow{OH^-} CH_3CHOHCH_2CHO$ 2 moles Acetaldehyde    3-Hydroxybutanal (an aldol)

$CH_3CHOHCH_2CHO \xrightarrow{dil.HCl, heat} CH_3CH=CHCHO + H_2O$

3-Hydroxybutanal    Crotonaldehyde

Reaction 2—Preparation of Acrylic Acid

Dehydrohalogenation of 2-chloropropanoic acid with strong base.

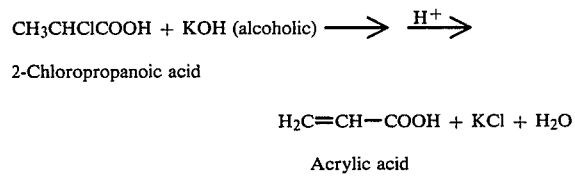

$CH_3CHClCOOH + KOH \text{(alcoholic)} \longrightarrow \xrightarrow{H^+}$

2-Chloropropanoic acid $H_2C=CH-COOH + KCl + H_2O$

Acrylic acid

Reaction 3—Preparation of Ethyl Acrylate

Dehydrohalogenation of ethyl 2-bromopropanoate with strong base.

$CH_3CHBrCOOCH_2CH_3 + NaOCH_2CH_3 \text{(ethanolic)} \rightarrow$ $CH_2=CHCOOCH_2CH_3 + NaBr + CH_3CH_2OH$ Reaction 4—Preparation of cinnamic acid from benzaldehyde and acetic anhydride using the Perkin reaction.

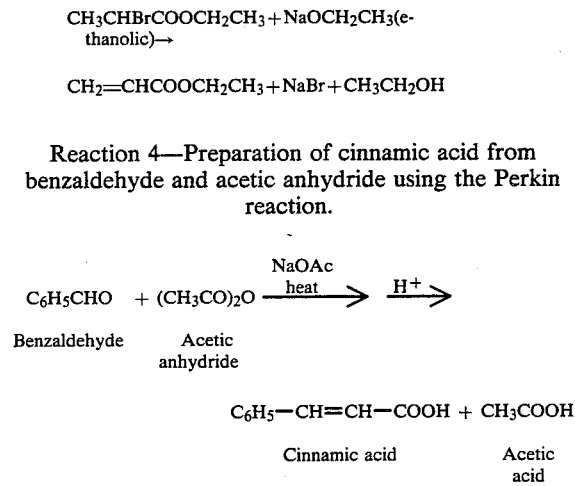

$C_6H_5CHO + (CH_3CO)_2O \xrightarrow[\text{heat}]{NaOAc} \xrightarrow{H^+}$

Benzaldehyde    Acetic anhydride $C_6H_5-CH=CH-COOH + CH_3COOH$

Cinnamic acid    Acetic acid

C. Preparation of Maleic Anhydride

Maleic anhydride is an industrially important raw material in the manufacture of alkyd and polyester resins, surface coatings, lubricant additives, plasticizers, copolymers, and agricultural chemicals. The predominant commercial route to maleic anhydride until recently was the vapor-phase oxidation of benzene over a supported catalyst containing vanadium oxides. However, the vapor-phase oxidation of butane over a supported catalyst containing phosphorus, vanadium, and oxygen is more efficient and is now the major route to maleic anhydride. Each of these processes is dependent upon a hydrocarbon-based feedstock.

Although not used commercially, various other processes for preparing maleic anhydride have been reported. For example, the conversion of fumaric acid to maleic anhydride in the presence of acetyl chloride is reported in Annschutz, R. and Bennert, C., "Contribution to the Knowledge of Monosubstituted Succinic Acids", *Ann.*, Volume 254, pp. 155-168 (1889). In the same article, the authors also reported the reaction of malic acid and acetyl chloride to form acetyl malic anhydride which, in turn, was decomposed thermally into maleic anhydride and acetic acid.

D. Preparation of Acrylic Acid

Acrylic acid is widely used to prepare acrylate polymer emulsions. These emulsions have found wide utility in the preparation of paints, floor polishes, and adhesives, and as coatings, finishes, and binders for leather, textiles, and paper. Various methods are used commercially to prepare acrylic acid. These methods include the oxidation of propylene, the hydrolysis of acrylonitrile, and the carbonylation of acetylene. Each of these methods is dependent upon a hydrocarbon-based feedstock.

SUMMARY OF THE INVENTION

The object of this invention is to provide an improved process for preparing alpha, beta-unsaturated carbonyl compounds. A more particular object is to provide a process for preparing all types of alpha, beta-unsaturated carbonyl compounds which: (1) is not necessarily dependent upon hydrocarbon-based feedstocks; (2) proceeds rapidly to completion under relatively mild conditions; (3) does not produce corrosive by-products; (4) employs recyclable reactants.

We have discovered a process for preparing alph, beta-unsaturated carbonyl compounds which comprises: (1) reacting an acid anhydride selected from the group consisting of glutaric anhydride and 3-alkyl-glutaric anhydride with a beta-hydroxy carbonyl compound having the following chemical formula:

R$_2$COH—CHR—CRO or R$_2$COH—CHR—CN where each R is any substituent group in the presence of a catalytically effective amount of an acid catalyst to form an ester; (2) reacting the ester in the presence of a catalytically effective amount of a base catalyst to form an alpha, beta-unsaturated carbonyl compound and a carboxylic acid; and (3) separating the alpha, beta-unsaturated carbonyl compound and the carboxylic acid.

This process offers many advantages over prior art processes. First of all, it is used to make all types of alpha, beta-unsaturated carbonyl compounds such as acids, anhydrides, aldehydes, ketones, esters, amides, and nitriles. Secondly, it is not dependent upon hydrocarbon-based feedstocks. For example, malic acid (which can be produced by the fermentation of glucose, a product of the acid and/or enzyme hydrolysis of starch) is used to produce maleic anhydride. Thirdly, the reaction proceeds rapidly to completion under relatively mild conditions. Fourthly, corrosive by-products are not formed. And fifthly, recyclable reactants are used.

DETAILED DESCRIPTION OF THE INVENTION

A. Process in General

This invention is a process for preparing alpha, beta-unsaturated carbonyl compounds. The process can be viewed as comprising three basic steps: (1) an acid-catalyzed esterification reaction; (2) a base-catalyzed beta elimination reaction; and (3) a separation. A fourth step including regeneration of the esterification reagent is also desirable.

More particularly, the first step of the process comprises reacting an acid anhydride with a beta-hydroxy carbonyl compound to form an ester. The acid anhydride is selected from the group consisting of glutaric anhydride and 3-alkylglutaric anhydride. The beta-hydroxy carbonyl compound has the following chemical formula:

R$_2$COH—CHR—CRO or R$_2$COH—CHR—CN where each R is any substituent group.

If the acid anhydride is glutaric anhydride, the acid-catalyzed esterification reaction can be represented as follows:

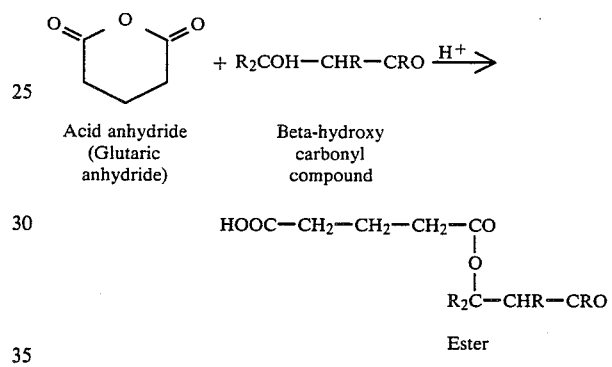

Acid anhydride (Glutaric anhydride)    Beta-hydroxy carbonyl compound

Ester

Depending upon the beta-hydroxy carbonyl compound chosen, the "R$_2$C—CHR—CRO" portion of the ester product may cyclize to form a cyclic anhydride.

The second step of the process comprises adding a catalytically effective amount of a base to the ester. The base catalyzes the elimination of the ester groups to form an alpha, beta-unsaturated carbonyl compound and a carboxylic acid. This step can be represented as follows:

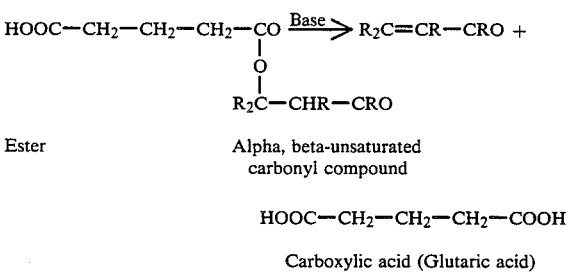

Ester    Alpha, beta-unsaturated carbonyl compound

HOOC—CH$_2$—CH$_2$—CH$_2$—COOH

Carboxylic acid (Glutaric acid)

As previously mentioned, the alpha, beta-unsaturated carbonyl compound formed may or may not be an anhydride.

The next step of the process comprises separating the alpha, beta-unsaturated carbonyl compound and the carboxylic acid. A further desirable step involves regeneration of the starting acid anhydride from the carboxylic acid. Alternatively, the alpha, beta-unsaturated carbonyl compound and the carboxylic acid might in other ways be modified as desired.

B. Acid Anhydride and Beta-Hydroxy Carbonyl Compound

The acid anhydride used in this process is selected from the group consisting of glutaric anhydride and 3-alkylglutaric anhydride. The substituent alkyl group generally contains 1 to about 5 carbon atoms. The alkyl group is preferably methyl or ethyl and is most preferably methyl. These anhydrides exhibit the unique combination of properties of being very reactive with the hydroxy carbonyl compounds in the acid-catalyzed esterification reaction and also being easily regenerated from their corresponding carboxylic acid. In contrast, other acid anhydrides do not combine these two properties as well. For example, acetic anhydride is very reactive in the esterification reaction, but is difficult to regenerate from acetic acid, whereas cis-1,2-cyclohexanedicarboxylic anhydride is easily regenerated from the acid, but is relatively unreactive in the esterification reaction. The preferred acid anhydride is 3-methylglutaric anhydride because of its ease of regeneration.

The choice of the beta-hydroxy carbonyl compound determines the identity of the alpha, beta-unsaturated carbonyl compound obtained. Table 1 illustrates some of the alpha, beta-unsaturated carbonyl compounds which are produced by this process and the corresponding beta-hydroxy carbonyl compounds employed as the starting materials.

TABLE 1

| Choice of Beta-Hydroxy Carbonyl Compound | |
|---|---|
| Desired Alpha, Beta-Unsaturated Carbonyl Compound | Beta-Hydroxy Carbonyl Compound to Use as Starting Material |
| $H_2C=C(CH_3)COOCH_3$ Methyl 2-methylpropenoate (Methyl methacrylate) | $CH_2OHCH(CH_3)COOCH_3$ Methyl 3-hydroxyl-2-methyl propanoate |
| $H_2C=CHCOOCH_2CH_3$ Ethyl propenoate (Ethyl acrylate) | $CH_2OHCH_2COOCH_2CH_3$ Ethyl 3-hydroxy-propanoate |
| $H_2C=CHCN$ Propenenitrile (Acrylonitrile) | $CH_2OHCH_2CN$ 3-Hydroxypropanenitrile |
| $H_2C=CHCHO$ Propenal (Acrolein) | $CH_2OHCH_2CHO$ 3-Hydroxypropanal |
| $CH_3CH=CHCHO$ 2-Butenal (Crotonaldehyde) | $CH_3CHOHCH_2CHO$ 3-Hydroxybutanal |
| $C_6H_5CH=CHCHO$ 3-Phenylpropenal (Cinnamaldehyde) | $C_6H_5CHOHCH_2CHO$ 3-Phenyl-3-hydroxy-propanal |
| $C_6H_5CH=CHC(O)CH_3$ 4-Phenyl-3-buten-2-one (Benzalacetone) | $C_6H_5CHOHCH_2C(O)CH_3$ 4-Phenyl-4-hydroxy-2-butanone |
| $H_2C=CHCOOH$ Propenoic acid (Acrylic acid) | $CH_2OHCH_2COOH$ 3-Hydroxypropanoic acid (Beta-hydroxypropionic acid) |
| $HC=CHC(O)OC(O)$ cis-Butenedioic anhydride (Maleic anhydride) | $HOOCCHOHCH_2COOH$ 2-Hydroxybutanedioic acid (Malic acid) |
| $HOOCCH=CHCOOH$ Butenedioic acid (Maleic or Fumaric acid) | $HOOCCHOHCH_2COOH$ 2-Hydroxybutanedioic acid (Malic acid) |

C. Acid-Catalyzed Esterification Reaction

As previously discussed, the first step of this invention is an acid-catalyzed esterification reaction between an acid anhydride and a beta-hydroxy carbonyl compound to produce an ester.

The molar ratio of the acid anhydride to the beta-hydroxy carbonyl compound is not critical. However, a molar excess of the acid anhydride is generally used when complete esterification of the hydroxy group is desired. Molar ratios of acid anhydride to hydroxy carbonyl compound of about 1:1 to 10:1 are preferred.

The acid catalyst may be organic or inorganic. Strong, relatively inexpensive, inorganic acids such as sulfuric acid and hydrochloric acid are most preferred.

The reaction is conducted at a temperature above the melting point of the anhydride. For example, if 3-methylglutaric anhydride is employed, the reaction temperature is greater than about 42° C. and when glutaric anhydride is used, the reaction temperature is at least 54° C. Increased temperatures increase the rate of the reaction. Reaction temperatures of about 50° to 150° C. are preferred.

The acid-catalyzed esterification reaction proceeds to completion relatively quickly, i.e., generally within two hours assuming a sufficient quantity of acid catalyst is used.

D. Base-Catalyzed Elimination Reaction

The second step of this invention is the base-catalyzed elimination reaction which converts the ester produced in the first step into an alpha, beta-unsaturated carbonyl compound and a carboxylic acid.

The base catalyst is preferably a salt of the carboxylic acid from which the acid anhydride is derived. This choice of base catalyst ensures that no additional anions are added to the reaction medium and, therefore, simplifies downstream separations. The sodium salt is most preferred because of its cost.

It is often preferable to employ a solvent in this reaction to reduce the viscosity of the reaction medium. Common nonprotic organic solvents, such as acetone, are preferred.

This reaction proceeds at room temperature, but higher temperatures may be employed if minimum reaction times are desired.

E. Separation and Further Processing

The various components in the product stream (including carboxylic acid, alpha, beta-unsaturated carbonyl compound, solvent, acid catalyst, base catalyst, and unreacted reactants) are routinely separated by conventional means. An especially important feature of this invention is that the carboxylic acid produced in the base-catalyzed esterification reaction (glutaric acid or 3-alkylglutaric acid) is easily regenerated to the corresponding acid anhydride. With this regeneration, the acid anhydride is conveniently re-used in the first step of this invention. The regeneration of the acid anhydride is generally accomplished by heating the carboxylic acid at a temperature of about 100° to 250° C. at a pressure less than about 50 mm mercury. The pressure is preferably less than about 15 mm mercury and most preferably less than about 5 mm mercury.

F. Examples

These examples are illustrative only. Unless otherwise indicated, temperature is expressed in units of degree Celsius, pressure in millimeters mercury, mass in grams, and percentage is computed based on weight.

EXAMPLE 1

This Example illustrates the acid-catalyzed esterification reaction of glutaric anhydride and malic acid to produce glutaryl malic anhydride (2-O-glutaryl-2- hydroxybutanedioic anhydride). This Example also illustrates the base-catalyzed elimination reaction of glutaryl malic anhydride to form maleic anhydride and glutaric acid and the isolation of the maleic anhydride.

The following were placed into a 250 ml round-bottom flask: (1) 97.0 g. of glutaric anhydride (0.85 moles); (2) 40.0 g. of malic acid (a racemic mixture of D and L forms) (0.3 moles); and 10 drops of concentrated sulfuric acid. The contents were stirred at 90° C. for 1.5 hours. A sample was withdrawn and analyzed by $^1$H NMR spectroscopy. The spectrum indicated that glutaryl malic anhydride had been formed in near-stoichiometric quantity.

The reaction mixture was then cooled to room temperature (approximately 20° C.) and diluted with 140 ml of acetone. At this point, 2.8 g. of sodium glutarate were added to catalyze the elimination reaction. The contents were stirred at room temperature for approximately 90 hours. A sample was withdrawn and analyzed by $^1$H NMR spectroscopy. The spectrum indicated that at least 95 mole percent of the glutaryl malic anhydride had been converted to maleic anhydride and glutaric acid.

The reaction mixture was then diluted with an additional 70 ml of acetone, the mixture filtered to remove insoluble sodium glutarate and the acetone removed by flash evaporation. The solid residue was placed in a 500 ml round-bottom flask fitted with a distilling head. A distillation was then carried out at 90° to 110° C. at a pressure of approximately 35 mm mercury. The solid distillate and solid residue were then analyzed by $^1$H NMR. The distillate was comprised of about 95 weight percent maleic anhydride. The residue was comprised of greater than 90 weight percent glutaric acid and glutaric anhydride.

EXAMPLE 2

This Example illustrates the acid-catalyzed esterification reaction of 3-methylglutaric anhydride and malic acid to produce 3-methylglutaryl malic anhydride [2-O-(3-methylglutaryl)-2-hydroxybutanedioic anhydride]. This Example also illustrates the base-catalyzed elimination reaction of 3-methylglutaryl malic anhydride to form maleic anhydride and 3-methylglutaric acid.

The following were placed into a 250 ml round-bottom flask: (1) 11.52 g. of 3-methylglutaric anhydride (0.09 moles); (2) 4.02 g. of malic acid (a racemic mixture of D and L forms) (0.03 moles); and 10 drops of concentrated sulfuric acid. The contents were stirred at 100° C. for 1.0 hour. A sample was withdrawn and analyzed by $^1$H NMR spectroscopy. The spectrum indicated that 3-methylglutaryl malic anhydride had been formed in near-stoichiometric quantity.

The reaction mixture was then cooled to room temperature (approximately 20° C.) and diluted with an equal volume of acetone. At this point, 2.0 g. of sodium 3-methylglutarate were added to catalyze the elimination reaction. The contents were stirred at room temperature for approximately 20 hours. A sample was withdrawn and analyzed by $^1$H NMR spectroscopy. The spectrum indicated that approximately 95 percent of the 3-methylglutaryl malic anhydride had been converted to maleic anhydride and 3-methylglutaric acid.

EXAMPLE 3

This Example illustrates that glutaric anhydride and 3-methylglutaric anhydride, in contrast to several other acid anhydrides, react with malic acid in the presence of an acid catalyst to form a malic anhydride ester.

The reactivity of an acid anhydride with malic acid was tested as follows. One mole of an acid anhydride, one-half mole (67 g.) of malic acid, and 2 ml of concentrated sulfuric acid were placed into a 500 ml flask and heated at 150° C. for 60 minutes. A sample was withdrawn and analyzed by $^1$H NMR spectroscopy for the presence of the malic anhydride ester.

The results of these experiments are presented below in Table 2.

TABLE 2

| Reactivity of Acid Anhydrides With Malic Acid | |
|---|---|
| Acid Anhydride | Reactivity |
| Glutaric | Reactive |
| 3-Methylglutaric | Reactive |
| Acetic | Reactive |
| Phthalic | Unreactive |
| Succinic | Unreactive |
| Homophthalic | Unreactive |
| Cis-1,2-cyclohexanedicarboxylic | Unreactive |

EXAMPLE 4

This Example illustrates that glutaric anhydride and 3-methylglutaric anhydride, in contrast to several other acid anhydrides, are regenerable from their corresponding carboxylic acids.

The regenerability of an acid anhydride was typically tested as follows. Twenty-five g. of the carboxylic acid corresponding to the desired acid anhydride were placed in a 100 ml flask and heated over the range of 100°–180° C. at a pressure of about 2 mm Hg for 2 hours. A sample of the distillate was withdrawn and analyzed by $^1$H NMR spectroscopy for the presence of the acid anhydride.

The results of these experiments are presented below in Table 3.

TABLE 3

| Regenerability of Acid Anhydride | |
|---|---|
| Carboxylic Acid | Approximate Mole Percent Anhydride Formed |
| Glutaric | 35 |
| 3-Methylglutaric | 90 |
| 2,2-Dimethylglutaric | <10 |
| Homophthalic | 80 |
| Cis-1,2-cyclohexanedicarboxylic | 90 |
| Acetic | Impractical |

We claim:

1. A process for preparing alpha, beta-unsaturated carbonyl compounds which comprises:
   (a) reacting an acid anhydride selected from the group consisting of glutaric anhydride and 3-methylglutaric anhydride with a beta-hydroxy carbonyl compound having the following chemical formula:

$R_2COH-CHR-CRO$ or $R_2COH-CHR-CN$ where each R is any substituent group, in the presence of a catalytically effective amount of an acid catalyst to form an ester;
   (b) reacting the ester in the presence of a catalytically effective amount of a base catalyst to form an alpha, beta-unsaturated carbonyl compound and a carboxylic acid;

(c) separating the alpha, beta-unsaturated carbonyl compound and the carboxylic acid;

(d) heating the carboxylic acid at a temperature of about 100° to 250° C. and at a pressure less than about 50 mm mercury to form the corresponding acid anhydride and water; and (e) isolating and recycling the acid anhydride.

2. The process of claim 1 wherein the hydroxy carbonyl compound is of the formula: $R_2COH-CHR-COOH$ or an ester thereof.

3. The process of claim 2 wherein the base catalyst comprises the sodium salt of the carboxylic acid from which the acid anhydride is derived.

4. The process of claim 3 wherein the acid anhydride comprises 3-methylglutaric anhydride.

5. The process of claim 4 wherein the beta-hydroxy carbonyl compound comprises malic acid such that the ester comprises 3-methylglutaryl malic anhydride and the alpha, beta-unsaturated carbonyl compound comprises maleic anhydride.

6. The process of claim 4 wherein the beta-hydroxy carbonyl compound comprises 3-hydroxypropanoic acid such that the ester comprises O-(3-methylglutaryl) 3-hydroxypropanoic acid, and the alpha, beta-unsaturated compound comprises acrylic acid.

7. The process of claim 4 wherein the beta-hydroxy carbonyl compound comprises methyl 3-hydroxy-2-methylpropanoate such that the ester comprises methyl O-(3-methylglutaryl)-3-hydroxy-2-methylpropanoate and the alpha, beta-unsaturated carbonyl compound comprises methyl methacrylate.

8. The process of claim 4 wherein the beta-hydroxy carbonyl compound comprises ethyl-3-hydroxypropanoate such that the ester comprises ethyl O-(3-methylglutaryl)-3-hydroxypropanoate and the alpha, beta-unsaturated carbonyl compound comprises ethyl acrylate.

* * * * *